United States Patent
Lin

(10) Patent No.: US 10,646,531 B2
(45) Date of Patent: May 12, 2020

(54) USES OF GRAPEFRUIT ESSENTIAL OIL IN INHIBITING INFLAMMATION ASSOCIATED WITH ALLERGIC DISEASE

(71) Applicant: TCI Co., Ltd., Taipei (TW)

(72) Inventor: Yung-Hsiang Lin, Taipei (TW)

(73) Assignee: TCI Co., Ltd., Taipei (TW)

( * ) Notice: Subject to any disclaimer, the term of this patent is extended or adjusted under 35 U.S.C. 154(b) by 0 days.

(21) Appl. No.: 16/158,429

(22) Filed: Oct. 12, 2018

(65) Prior Publication Data

US 2019/0111097 A1   Apr. 18, 2019

Related U.S. Application Data

(60) Provisional application No. 62/573,929, filed on Oct. 18, 2017.

(30) Foreign Application Priority Data

Sep. 19, 2018   (TW) .............................. 107133011 A

(51) Int. Cl.
*A61K 36/752*   (2006.01)
*A61P 29/00*   (2006.01)
*A61P 35/00*   (2006.01)

(52) U.S. Cl.
CPC ............ *A61K 36/752* (2013.01); *A61P 29/00* (2018.01); *A61P 35/00* (2018.01)

(58) Field of Classification Search
None
See application file for complete search history.

(56) References Cited

U.S. PATENT DOCUMENTS 6,579,543 B1 *   6/2003   McClung ............... A61K 8/345
424/401
2019/0328013 A1 *   10/2019   Legge ..................... A23L 33/12

FOREIGN PATENT DOCUMENTS

CN   109528576   *   3/2019

OTHER PUBLICATIONS de la Garza, A. et al. Helichrysum and Grapefruit Extracts Boost Weight Loss in Overweight Rats Reducing Inflammation. J of Medicinal Foods 18(8)890-898, 2015. (Year: 2015).*
Lee, Jun Won et al., "IL-3 Expression by Myeloma Cells Increases Both Osteoclast Formation and Growth of Myeloma Cells", Blood Journal, Mar. 15, 2005, vol. 103, No. 6, pp. 2308-2315.
Zheng, Xueyan et al., "Interleukin-3, but Not Granulocyte-Macrophage Colony-Stimulating Factor and Interleukin-5, Inhibits Apoptosis of Human Basophils Through Phosphatidylinositol 3-Kinase; Requirement of Nf-kB-Dependent and—Independent Pathways", Immunology, 2002, vol. 107, pp. 306-315.

* cited by examiner

*Primary Examiner* — Ralph J Gitomer
(74) *Attorney, Agent, or Firm* — Christensen, Fonder, Dardi & Herbert PLLC

(57) ABSTRACT

A method for at least one of inhibiting growth of myeloma cells, inhibiting myeloma cell-induced activation or formation of osteoclasts, and inhibiting inflammation is provided, wherein the method comprises administering to a subject in need an effective amount of grapefruit essential oil.

4 Claims, 1 Drawing Sheet

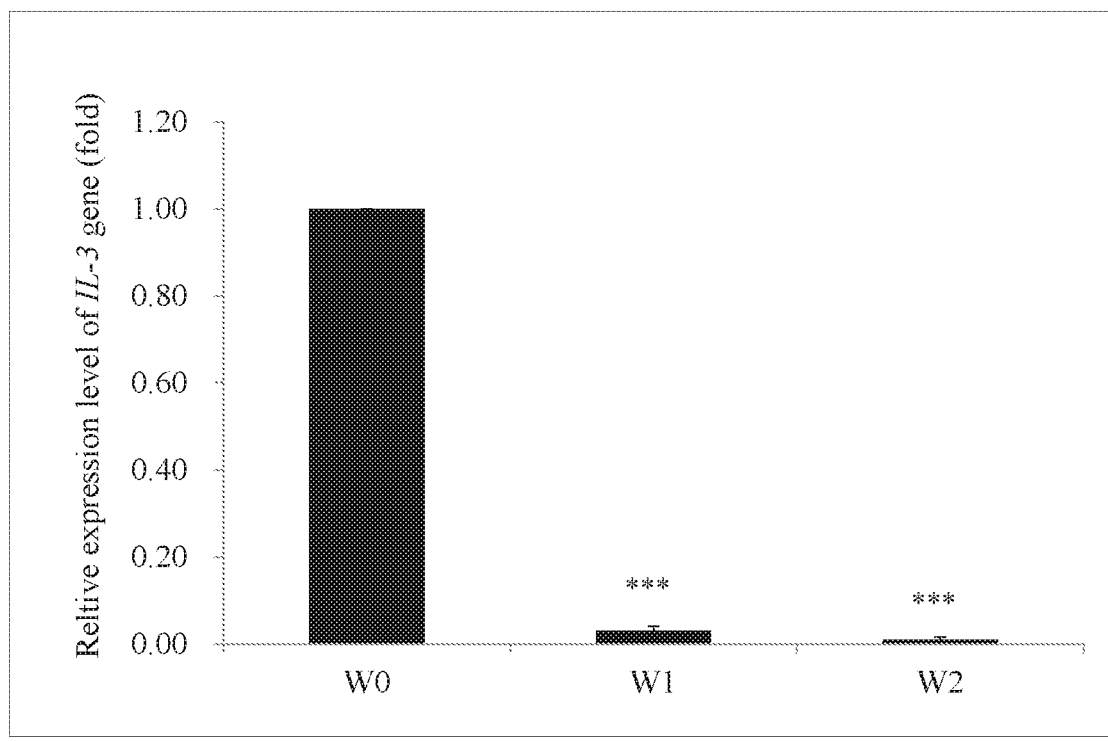

USES OF GRAPEFRUIT ESSENTIAL OIL IN INHIBITING INFLAMMATION ASSOCIATED WITH ALLERGIC DISEASE

CROSS REFERENCE TO RELATED APPLICATIONS

This application claims priority to U.S. Provisional Application Ser. No. 62/573,929 filed on Oct. 18, 2017, and to Taiwan Patent Application No. 107133011 filed on Sep. 19, 2018, the disclosure of which are incorporated herein in its entirety by reference.

FIELD OF THE INVENTION

The present invention relates to the use of grapefruit essential oil, including the use of grapefruit essential oil in inhibiting growth of myeloma cells, inhibiting myeloma cell-induced activation or formation of osteoclasts, and/or inhibiting inflammation. The present invention also relates to the use of grapefruit essential oil in delaying progression of myeloma, extending lifespan of myeloma patients, inhibiting myeloma-induced bone destruction, relieving bone pain of myeloma patients, and/or reducing fracture risk in myeloma patients. The present invention also relates to the use of grapefruit essential oil in decreasing expression of IL-3 gene.

BACKGROUND OF THE INVENTION

Multiple myeloma (MM) is a hematologic malignancy resulting from the abnormal proliferation of plasma cells within the bone marrow. It was revealed by researches that the cause of multiple myeloma might be relevant to inheritance or the exposure of hazardous materials (e.g., chemicals and radiation) in the environment, but is still unclear.

In most cases of multiple myeloma patients, no symptom would be observed at the initial stage. However, along with the progression of multiple myeloma, myeloma cells will creep and gather in the marrow or on the solid part(s) of the both ends of bone so as to form multiple masses. The masses will activate osteoclasts to invade and damage multiple areas of bone, result in bone pain and multiple tumor lesions. In clinic, common symptoms of multiple myeloma include anaemia, bone pain, fracture easily, hypercalcemia, kidney failure, etc.

Inventors of the present invention incidentally discovered that grapefruit essential oil can effectively decrease the expression of IL-3 gene, and thus, is effective in inhibiting growth of myeloma cells, inhibiting myeloma cell-induced activation or formation of osteoclasts, and inhibiting inflammation. Hence, grapefruit essential oil can be used for delaying progression of myeloma, extending lifespan of myeloma patients, inhibiting myeloma-induced bone destruction, relieving bone pain of myeloma patients, and/or reducing fracture risk in myeloma patients.

SUMMARY OF THE INVENTION

An objective of the present invention is to provide a use of grapefruit essential oil in the manufacture of a pharmaceutical composition for inhibiting growth of myeloma cells, inhibiting myeloma cell-induced activation or formation of osteoclasts, and/or inhibiting inflammation. Preferably, the pharmaceutical composition is for delaying progression of myeloma, extending lifespan of myeloma patients, inhibiting myeloma-induced bone destruction, relieving bone pain of myeloma patients, reducing fracture risk in myeloma patients, treating myeloma, and/or inhibiting inflammation associated with allergic disease. Preferably, the myeloma is multiple myeloma, and the allergic disease is as least one of asthma and allergic rhinitis. Preferably, the pharmaceutical composition is provided in a form for oral administration, inhalation administration, or transdermal administration.

Another objective of the present invention is to provide a use of grapefruit essential oil in the manufacture of a pharmaceutical composition for decreasing expression of IL-3 gene. Preferably, the pharmaceutical composition is provided in a form for oral administration, inhalation administration, or transdermal administration.

Still another objective of the present invention is to provide a pharmaceutical composition for inhibiting growth of myeloma cells, inhibiting myeloma cell-induced activation or formation of osteoclasts, and/or inhibiting inflammation. The pharmaceutical composition comprises an effective amount of grapefruit essential oil. Preferably, the pharmaceutical composition is for delaying progression of myeloma, extending lifespan of myeloma patients, inhibiting myeloma-induced bone destruction, relieving bone pain of myeloma patients, reducing fracture risk in myeloma patients, treating myeloma, and/or inhibiting inflammation associated with allergic disease. Preferably, the myeloma is multiple myeloma, and the allergic disease is as least one of asthma and allergic rhinitis. Preferably, the pharmaceutical composition is provided in a form for oral administration, inhalation administration, or transdermal administration.

Yet another objective of the present invention is to provide a pharmaceutical composition for decreasing expression of IL-3 gene. The pharmaceutical composition comprises an effective amount of grapefruit essential oil. Preferably, the pharmaceutical composition is provided in a form for oral administration, inhalation administration, or transdermal administration.

Yet another objective of the present invention is to provide a method for at least one of inhibiting growth of myeloma cells, inhibiting myeloma cell-induced activation or formation of osteoclasts, and inhibiting inflammation, comprising administering to a subject in need an effective amount of grapefruit essential oil. In the method of the present invention, the grapefruit essential oil can be administered to the subject as the pharmaceutical composition described above. Preferably, the method in accordance with the present invention is for at least one of delaying progression of myeloma, extending lifespan of myeloma patients, inhibiting myeloma-induced bone destruction, relieving bone pain of myeloma patients, reducing fracture risk in myeloma patients, treating myeloma, and inhibiting inflammation associated with allergic disease. Preferably, the myeloma is multiple myeloma, and the allergic disease is as least one of asthma and allergic rhinitis.

Yet another objective of the present invention is to provide a method for decreasing expression of IL-3 gene, comprising administering to a subject in need an effective amount of grapefruit essential oil. In the method of the present invention, the grapefruit essential oil can be administered to the subject as the pharmaceutical composition described above.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

FIG. 1 shows the influence of grapefruit essential oil on the expression of IL-3 gene in peripheral blood mononuclear cells (PBMCs), wherein the result of "W0" group refers to the expression level before the administration of grapefruit essential oil, and the results of "W1" group and "W2" group refer to the expression levels after the continuous administration of grapefruit essential oil for one week and two weeks, respectively (*** represents the result is significantly different from that of the "W0" group, p<0.001).

DESCRIPTION OF THE PREFERRED EMBODIMENTS

The following will describe some of the embodiments of the present invention in detail. However, without departing from the spirit of the present invention, the present invention may be embodied in various embodiments and should not be limited to the embodiments described in the specification or defined in the appended claims.

In addition, unless otherwise indicated herein, the expressions "a," "an," "the," or the like recited in the specification of the present invention (especially in the claims) are intended to include both the singular and plural forms. The term "treat" or "treating" used in this specification should not be construed as treating a subject until the subject completely recovered, but should include maintaining the progression or symptoms of the diseases in a substantially static state, increasing the recovery rate of a subject, alleviating the severity of a particular condition of illness, or increasing the life quality of patients. The term "subject" recited in this specification refers to a mammalian, including human and non-human animals.

Research results have shown that an overexpression of IL-3 gene may increase the growth of myeloma cells, which may induce the activation or formation of osteoclasts, and these can be noted in "IL-3 expression by myeloma cells increases both osteoclast formation and growth of myeloma cells. *Blood.* 2004 Mar. 15; 103(6):2308-15," which is entirely incorporated hereinto by reference. Furthermore, research results have also shown that a decrement in the expression of IL-3 gene can lead to an inhibition of inflammation effectively, especially inhibiting the inflammation associated with allergic diseases, and these can be noted in "Interleukin-3, but not granulocyte-macrophage colony-stimulating factor and interleukin-5, inhibits apoptosis of human basophils through phosphatidylinositol 3-kinase: requirement of NF-κB-dependent and—independent pathways. *Immunology.* 2002 Aug. 2; 107:306-315," which is entirely incorporated hereinto by reference.

Therefore, if the expression of IL-3 gene can be inhibited effectively, the following effects could be provided: inhibiting growth of myeloma cells, inhibiting myeloma cell-induced activation or formation of osteoclasts, and inhibiting inflammation.

Essential oil is an oil product containing aromatic compound(s) and is extracted from plants. Specifically, essential oil can be provided by extracting the flowers, leaves, roots, seeds, peels, fruits and/or stems of plant(s) by such as distillation, expeller press, solvent extraction, enfleurage, and supercritical fluid extraction (SFE). Depending on the species and parts of plant(s) from which the essential oil is produced, the essential oil may have different effects and can be used in different forms in daily life or in the pharmaceutical industry as well.

Grapefruit, a common fruit, is a subtropical plant belonging to the Rutaceae family and *Citrus* genus. Grapefruit essential oil usually smells like citrus fruit, and is known to be effective in relieving stress and distress, helping keep oily skin clean, promoting hair growth, treating acne, reducing body weight and diuresis.

Inventors of the present invention incidentally discovered that grapefruit essential oil can effectively decrease the expression of IL-3 gene. Therefore, the present invention relates to the use of grapefruit essential oil, including: using grapefruit essential oil in manufacturing a pharmaceutical composition, providing a pharmaceutical composition containing an effective amount of grapefruit essential oil, and providing a method of administering a subject in need an effective amount of the aforementioned pharmaceutical composition. The pharmaceutical composition provided in accordance with the present invention is for at least one of inhibiting growth of myeloma cells, inhibiting myeloma cell-induced activation or formation of osteoclasts, and inhibiting inflammation. Preferably, the pharmaceutical composition provided in accordance with the present invention is for at least one of delaying progression of myeloma, extending lifespan of myeloma patients, inhibiting myeloma-induced bone destruction, relieving bone pain of myeloma patients, reducing fracture risk in myeloma patients, treating myeloma, and inhibiting inflammation associated with allergic disease. In particular, the myeloma is multiple myeloma, and the allergic disease is asthma or allergic rhinitis. Furthermore, the pharmaceutical composition and method provided in accordance with the present invention are also for decreasing expression of IL-3 gene.

The grapefruit essential oil adopted by the present invention could be obtained from any suitable source. For example, the grapefruit essential oil could be obtained by extracting grapefruit (e.g., extracting grapefruit skin via expeller press), and could be purchased from the market.

The pharmaceutical composition provided in accordance with the present invention could be administered to a subject in need systemically or topically, and could be delivered by various drug delivery systems (DDSs), such as oral drug delivery system, transdermal drug delivery system, inhalation drug delivery system, etc. For example, to enhance bioavailability, control drug release speed, target the lesion precisely and reduce side effects, the pharmaceutical composition could be delivered by a liposome, a microcapsule, nanoparticles, or microneedles, but is not limited thereby.

Depending on the desired purpose(s), the pharmaceutical composition of the present invention could be provided in any suitable form without particular limitations. For example, the pharmaceutical composition could be provided in a form for oral administration, inhalation administration, or transdermal administration, but is not limited thereby. Depending on the form and purpose(s), a suitable carrier could be chosen and used to provide the pharmaceutical composition. Examples of the carrier include excipients, diluents, auxiliaries, stabilizers, absorption enhancers, disintegrating agent, hydrotropic agents, emulsifiers, antioxidants, adhesives, binders, tackifiers, dispersants, suspending agents, lubricants, hygroscopic agents, etc.

As a form for oral administration, the pharmaceutical composition of the present invention could comprise any pharmaceutically acceptable carrier that will not adversely affect the desired effects of the active ingredient (i.e., grapefruit essential oil). Examples of the carrier include, but are not limited to, water, saline, dextrose, glycerol, ethanol or its analogs, oil (e.g., olive oil, castor oil, cottonseed oil, peanut oil, corn oil, and germ oil), polyethylene glycol, and combinations thereof. The pharmaceutical composition could be provided by any suitable method in any suitable form for oral administration, such as in the form of a capsule, a fluidextract, a solution, syrup, a suspension, a tincture, or an elixir, but is not limited thereby.

As a form for inhalation administration, the pharmaceutical composition of the present invention could be optionally aerosolized by any suitable approach to facilitate the entry of the pharmaceutical composition into the respiratory tract. For example, the pharmaceutical composition could be administered through a nebulizer, an aroma burner, an evaporative diffuser, an aroma lamp, an aroma diffuser, an essential oil candle, or an essential oil necklace, but is not limited thereby.

As a form for transdermal administration, the pharmaceutical composition of the present invention could also comprise any pharmaceutically acceptable carrier that will not adversely affect the desired effects of the active ingredient (i.e., grapefruit essential oil). Examples of the carrier include, but are not limited to, water, mineral oil, propylene glycol, polyethylene oxide, liquid petrolatum, sorbitan monosterate, and polysorbate 60. The pharmaceutical composition could be provided by any suitable method in any suitable form for transdermal administration, such as in the form of an emulsion (such as a massage emulsion), a cream (such as a massage cream), an oil (such as a massage oil), a gel (such as a hydrogel), a paste (such as a dispersing paste, an ointment), a lotion, a spray, a patch (such as a microneedle patch), etc., but is not limited thereby.

Optionally, the pharmaceutical composition provided in accordance with the present invention could further comprise a suitable amount of additives, such as a flavoring agent, a toner, or a coloring agent for enhancing the palatability and the visual perception of the pharmaceutical composition, and/or a buffer, a conservative, a preservative, an antibacterial agent, or an antifungal agent for improving the stability and storability of the pharmaceutical composition. Optionally, the pharmaceutical composition could further comprise one or more other active ingredients, or to be used in combination with a medicament comprising one or more other active ingredients, to further enhance the effects of the pharmaceutical composition, or to increase the application flexibility and adaptability of the preparation thus provided, as long as the other active ingredients will not adversely affect the desired effects of the active ingredient of the present invention (i.e., grapefruit essential oil).

Depending on the needs, age, body weight and health conditions of the subject as well as the purpose(s), the pharmaceutical composition provided in accordance with the present invention could be dosed at various administration frequencies, such as once a day, multiple times a day, once every few days, etc. In addition, the concentration of grapefruit essential oil in the pharmaceutical composition could be adjusted depending on the requirements of practical application.

As described above, the present invention also provides a method for at least one of inhibiting growth of myeloma cells, inhibiting myeloma cell-induced activation or formation of osteoclasts, and inhibiting inflammation, comprising administering to a subject in need an effective amount of grapefruit essential oil, wherein the term "a subject in need" refers to a subject suffering from myeloma, a subject with high risk of myeloma, a subject whose osteoclast is overly activated or overly formed, and/or a subject suffering from allergic disease(s). The present invention also relates to a method for decreasing expression of IL-3 gene, comprising administering to a subject in need an effective amount of grapefruit essential oil, wherein the term "a subject in need" refers to a subject whose IL-3 gene is overexpressed. In the method in accordance with the present invention, the grapefruit essential oil could be administered to the subject in need as a pharmaceutical composition and the administration type, administration route, administration form, administration frequency and uses of the pharmaceutical composition are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Example 1: Effect of Grapefruit Essential Oil on Decreasing Expression of IL-3 Gene (1-1) Collection of Blood Samples The following two-week trial was conducted on six persons (six subjects) to understand the effects of grapefruit essential oil on human body. During the trial, each subject wore an essential oil necklace containing grapefruit essential oil (purchased from New Directions Australia) for 8 hours every day, and the essential oil necklace was added with 20 µL of grapefruit essential oil at nine o'clock every morning to ensure that the amount of essential oil in the necklace was sufficient. And, 6 mL blood sample was collected from each subject prior to the trial (i.e., prior to starting wearing the essential oil necklace containing grapefruit essential oil; hereinafter referred to as "W0" group), after starting the trial for one week (i.e., wearing the essential oil necklace containing grapefruit essential oil eight hours a day and for one week; hereinafter referred to as "W1" group), and after starting the trial for two weeks (i.e., wearing the essential oil necklace containing grapefruit essential oil eight hours a day and for two weeks; hereinafter referred to as "W2" group), respectively, by using blood collection tubes that contained ethylenediaminetetraacetic acid (EDTA) (purchased from Greiner Bio-One International, product number: 456036). The blood samples thus obtained were used for the following experiments and analysis.

(1-2) Isolation of Peripheral Blood Mononuclear Cells (PBMCs)

The blood samples of "W0" group, "W1" group and "W2" group obtained from Example (1-1) were individually subjected to the following steps to isolate PBMCs from the blood samples of each group:

1. Injecting each blood sample to a 15 mL centrifuge tube, and subjecting the centrifuge tube to a centrifugation at 300 g for 15 minutes (the centrifugation was stopped by natural deceleration);
2. Removing the upper blood plasma layer, taking out 2 mL of buffy coat from the remnant and putting the same to another 15 mL centrifuge tube, and then adding thereinto 2 mL of phosphate buffered saline (PBS) and mixing evenly to provide a diluted buffy coat;
3. Tilting another 15 mL centrifuge tube loaded with 3 mL of Ficoll-Plague Plus (purchased from Sigma-Aldrich, product number: GE17-1440-03) for about 45 degrees, then slowly adding the diluted buffy coat provided by step 2 into the centrifuge tube and carefully returning the centrifuge tube back to the vertical situation, so that the buffy coat and Ficoll-Plague Plus were layered (not mixed), and then, subjecting the centrifuge tube to a centrifugation at 400 g for 40 minutes (the centrifugation was stopped by natural deceleration);

4. Removing the upper liquid layer, taking out 2 mL to 3 mL of the middle layer (i.e., mononuclear cell layer) and putting the same to a new 15 mL centrifuge tube, then, washing the cells with PBS three to five times, and then, subjecting the washed cells to a centrifugation at 300 g for 10 minutes; and
 5. Removing the remaining PBS to provide the precipitate, i.e., the PBMCs of "W0" group, "W1" group, or "W2" group.

(1-3) Gene Expression Analysis

The PBMCs of "W0" group, "W1" group and "W2" group obtained from Example (1-2) were lysed by an RNA lysis buffer (RB buffer; purchased from Geneaid company). Thereafter, the PBMC lysate of each group was subjected to an RNA extraction with an RNA extraction kit (purchased from Geneaid company), and then the RNA was transcribed into cDNA with a reverse transcriptase (SuperScript® III Reverse Transcriptase; purchased from Invitrogen company). Then, the cDNA of each group was subjected to a quantitative polymerase chain reaction (qPCR) by using an ABI Step One Plus system and a KAPA SYBR FAST qPCR kit to determine the expression level of IL-3 gene in the cells of each group. Finally, the data was analyzed by T.TEST of Excel (one tailed Student's t-test), and the analysis result of "W0" group was used as a basis (i.e., the gene expression of "W0" group was set as 1-fold) to calculate the relative gene expression level of "W1" group and that of "W2" group. The results are shown in FIG. 1.

As shown in FIG. 1, as compared to "W0" group, the expression levels of IL-3 gene in the cells of "W1" group and "W2" group significantly decreased. These results indicate that grapefruit essential oil can effectively decrease the expression of IL-3 gene, and thus, is effective in inhibiting growth of myeloma cells, inhibiting myeloma cell-induced activation or formation of osteoclasts, and inhibiting inflammation. Hence, grapefruit essential oil can be used for delaying progression of myeloma, extending lifespan of myeloma patients, inhibiting myeloma-induced bone destruction, relieving bone pain of myeloma patients, and/or reducing fracture risk in myeloma patients.

What is claimed is:

1. A method for inhibiting inflammation associated with allergic disease, consisting of administering to a subject suffering from allergic disease an effective amount of grapefruit essential oil or an effective amount of a composition consisting of (i) grapefruit essential oil and (ii) at least one of water, saline, dextrose, ethanol, polyethylene glycol, propylene glycol, polyethylene oxide, liquid petrolatum, sorbitan monosterate, polysorbate 60, a flavoring agent, a toner, a coloring agent, buffer, a conservative, a preservative, an antibacterial agent and an antifungal agent.

2. The method as claimed in claim 1, wherein the allergic disease is as least one of asthma and allergic rhinitis.

3. The method as claimed in claim 1, wherein the grapefruit essential oil or the composition is administered to the subject by at least one of oral administration, inhalation administration, and transdermal administration.

4. The method as claimed in claim 2, wherein the grapefruit essential oil or the composition is administered to the subject by at least one of oral administration, inhalation administration, and transdermal administration.

\* \* \* \* \*